(12) United States Patent
Kaeseberg et al.

(10) Patent No.: US 12,137,984 B2
(45) Date of Patent: Nov. 12, 2024

(54) TECHNIQUE OF DETERMINING A POSE OF A SURGICAL REGISTRATION DEVICE

(71) Applicant: Stryker European Operations Limited, Carrigtwohill (IE)

(72) Inventors: Marc Kaeseberg, Biesenthal (DE); Christopher Oezbek, Berlin (DE); Markus Finke, Berlin (DE); Christian Winne, Berlin (DE)

(73) Assignee: Stryker European Operations Limited, Carrigtwohill (IE)

( * ) Notice: Subject to any disclaimer, the term of this patent is extended or adjusted under 35 U.S.C. 154(b) by 698 days.

(21) Appl. No.: 17/142,341

(22) Filed: Jan. 6, 2021

(65) Prior Publication Data

US 2021/0212768 A1 Jul. 15, 2021

(30) Foreign Application Priority Data

Jan. 9, 2020 (EP) .................................... 20151023

(51) Int. Cl.
*A61B 34/20* (2016.01)
*A61B 90/92* (2016.01)
(Continued)

(52) U.S. Cl.
CPC .............. *A61B 34/20* (2016.02); *A61B 90/92* (2016.02); *A61B 90/96* (2016.02); *G06T 7/70* (2017.01);
(Continued)

(58) Field of Classification Search
CPC . A61B 2034/2055; A61B 34/20; A61B 90/92; A61B 90/96; A61B 2034/2065;
(Continued)

(56) References Cited

U.S. PATENT DOCUMENTS

| 2005/0203380 | A1 | 9/2005 | Sauer et al. |
| 2016/0171703 | A1 | 6/2016 | Rhee et al. |

(Continued)

FOREIGN PATENT DOCUMENTS

| EP | 3441788 A1 | 2/2019 |
| WO | 0134050 A2 | 5/2001 |

(Continued)

OTHER PUBLICATIONS

English language abstract for WO 2006/131373 A2 extracted from espacenet.com database on Jan. 21, 2021, 2 pages.

*Primary Examiner* — Aaron F Roane
(74) *Attorney, Agent, or Firm* — Howard & Howard Attorneys PLLC

(57) ABSTRACT

A method, a surgical registration device, a sensor device, a system, a computer program, a computer-readable medium and a data carrier signal are disclosed. The surgical registration device comprises a surface, an optical pattern on the surface, and an interface unit to attach to a tracking system. The method comprises obtaining an image of the surgical registration device, detecting the at least one optical pattern in the image, obtaining surface model data describing the surface, obtaining a location of the optical pattern with respect to the surface, determining, based on the detected optical pattern, the surface model data and the location of the optical pattern, a second pose of the surface, obtaining depth information describing three-dimensional coordinates of the surface and determining, based on the second pose, the surface model data and the depth information, a third pose of the surface of the surgical registration device.

14 Claims, 11 Drawing Sheets

(51) Int. Cl.
*A61B 90/96* (2016.01)
*G06T 7/70* (2017.01)
*G06T 7/73* (2017.01)
*G16H 20/40* (2018.01)
*G16H 30/40* (2018.01)
*A61B 90/00* (2016.01)

(52) U.S. Cl.
CPC ............... *G06T 7/73* (2017.01); *G06T 7/74* (2017.01); *G16H 20/40* (2018.01); *G16H 30/40* (2018.01); *A61B 2034/2055* (2016.02); *A61B 2034/2065* (2016.02); *A61B 2034/2068* (2016.02); *A61B 2090/3937* (2016.02); *G06T 2207/10024* (2013.01); *G06T 2207/10028* (2013.01)

(58) Field of Classification Search
CPC .... A61B 2034/2068; A61B 2090/3937; G06T 7/73; G06T 7/74; G06T 7/70; G16H 20/40; G16H 30/40

USPC .......................................................... 606/1
See application file for complete search history.

(56) References Cited

U.S. PATENT DOCUMENTS

| | | |
|---|---|---|
| 2016/0225192 A1 | 8/2016 | Jones et al. |
| 2018/0185100 A1 | 7/2018 | Weinstein et al. |
| 2019/0209080 A1* | 7/2019 | Gullotti ............ A61B 17/7035 |

FOREIGN PATENT DOCUMENTS

| | | |
|---|---|---|
| WO | 2006131373 A2 | 12/2006 |
| WO | 2016066287 A1 | 5/2016 |
| WO | 2018063528 A1 | 4/2018 |
| WO | 2019040493 A1 | 2/2019 |
| WO | 2019113334 A1 | 6/2019 |

* cited by examiner

TECHNIQUE OF DETERMINING A POSE OF A SURGICAL REGISTRATION DEVICE

PRIORITY CLAIM

This application claims priority under 35 U.S.C. § 119 to European Patent Application No. 20151023.7, filed Jan. 9, 2020, the entire contents of which are hereby incorporated by reference.

TECHNICAL FIELD

The present disclosure generally relates to surgical navigation, namely to a surgical registration device and a method of determining a pose thereof. In particular, a method, a computer program, a computer-readable medium, a data carrier signal, a processor, a sensor device, a surgical navigation system and a surgical registration device are disclosed.

BACKGROUND

Many surgical procedures benefit from determining positions and orientations of surgical objects, such as surgical instruments and a patient, as a basis for providing navigation instructions to a surgeon. Surgical navigation often requires initially registering three dimensional image data of a surgical object in a coordinate system of a surgical navigation system. During registration, the three dimensional image data is arranged and oriented in the coordinate system relative to a tracking marker associated with the surgical object (i.e. a patient or a surgical instrument), which subsequently allows determining changes in the position and orientation of the three dimensional image data in the coordinate system by tracking movements of the tracking marker.

In an exemplary application of a surgical navigation system, a surgical instrument and the patient are each associated with a tracking marker, wherein three dimensional image data previously obtained by, for example, a computer tomography (CT) scan is registered with the patient tracking marker and three dimensional image data of the surgical instrument is registered with the instrument tracking marker. By tracking the tracking markers of the patient and the surgical instrument, the position and orientation of both surgical objects and a spatial relationship between the three dimensional image data of the surgical instrument and of the patient can be determined. The determined spatial relationship can, for example, be displayed on a screen, helping the surgeon guide the surgical instrument relative to the patient.

During surgery, a plurality of tracking types (i.e., optical tracking, electromagnetic tracking or ultrasonic tracking) may be used in parallel or one after the other. For example, an electromagnetic tracking system and an optical tracking system may be used in combination. In such a case, the surgeon may select the tracking type that best suits the task at hand.

Sensor devices have been described which include an image sensor and a depth sensor. For example, head-mounted augmented reality devices including a camera and a time of flight camera have been disclosed. Such sensor devices may be used as the optical tracking system in surgical navigation. Alternatively or additionally, such sensor devices may be equipped with a display in order to allow an augmented view of a surgical site superimposed with the navigation instructions. For the augmented view to be accurate, a relative spatial relationship between a tracking system of the surgical navigation system, for example the electromagnetic tracking system, and the sensor device needs to be determined as precisely as possible.

Surgical registration devices haven been disclosed which are detectable by both an optical tracking system and an electromagnetic tracking system in order to allow a determination of the relative spatial relationship between the two tracking systems.

The aforementioned sensor devices typically are intended for consumer applications. Therefore, an accuracy of a position and orientation of a surgical registration device as determined by such sensor devices is often quite low, resulting in a low tracking accuracy and a low accuracy of the determined relative spatial relationship between the electromagnetic tracking system and the sensor device.

SUMMARY

There is a need for a technique of determining a pose of a surgical registration device that solves one or more of the aforementioned or other problems.

According to a first aspect, a computer-implemented method of determining a pose of a surgical registration device is provided, wherein the surgical registration device comprises a surface and at least one optical pattern arranged on the surface. The method comprises obtaining an image of at least a first part of the surgical registration device in a first pose, and detecting the at least one optical pattern in the image. The method also comprises obtaining surface model data describing a surface of at least a second part of the surgical registration device and obtaining first location information indicating a location of the at least one optical pattern with respect to the surface of the surgical registration device. The method of the first aspect comprises determining, based on the detected at least one optical pattern, the surface model data and the first location information, a second pose of the surface of the surgical registration device. The method further comprises obtaining depth information describing three-dimensional coordinates of the surface of at least the second part of the surgical registration device in the first pose, and determining, based on the second pose, the surface model data and the depth information, a third pose of the surface of the surgical registration device.

The first part of the surgical registration device may be equal to the second part of the surgical registration device. In another variant, the first part of the surgical registration device is different from the second part of the surgical registration device. Alternatively, the first part of the surgical registration device may at least partially overlap with the second part of the surgical registration device, in other words, the first part of the surgical registration device may comprise a portion which is also comprised in the second part of the surgical registration device.

The first pose of the surgical registration device can be referred to as the real pose of the surgical registration device. The first pose of the surgical registration device may be a first position and orientation of the surgical registration device in a given coordinate system. The second pose of the surgical registration device is for example a second position and orientation of the surgical registration device in the given coordinate system. The third pose of the surgical registration device is for example a third position and orientation of the surgical registration device in the given coordinate system. The given coordinate system may be an internal coordinate system of a sensor device, such as a sensor device coordinate system.

The depth information is for example obtained by a sensor of a sensor device, for example by a depth sensor comprising a time of flight camera or a stereo camera. The depth information may comprise depth pixels or be determined based on depth pixels obtained by the sensor of the sensor device. For example, the depth information describes a three-dimensional mesh representing at least a part of the surface of the surgical registration device, for example the surface of at least the second part of the surgical registration device. The depth information may describe a point cloud, wherein each point defines a three-dimensional coordinate representing a point on the surface of the surgical registration device, for example a point on the surface of at least the second part of the surgical registration device. The depth information in one example describes a depth image comprising a plurality of depth image pixels. Each of the depth image pixels may contain a depth value describing the distance of an object depicted by the respective depth image pixel to the sensor of the sensor device.

The optical pattern is for example a two-dimensional pattern such as an arrangement of graphical symbols, a barcode, a data matrix code, a quick response (QR) code, a PDF417 code, a MaxiCode, an AZTEC code or else. The optical pattern is in one variant a pattern formed in black and white only, nevertheless, the optical pattern may comprise at least one element having a color.

Determining the third pose may comprise determining, based on the second pose and based on the surface model data, a surface model describing the surface of at least the second part of the surgical registration device in the second pose, and matching the surface model to the depth information to determine the third pose.

The surface model is for example matched to a part of the depth information which fulfills at least one criterion chosen from:
  not representing a predetermined surface attribute;
  not representing an object other than the surgical registration device; and
  not representing a part of the surgical registration device which has a predetermined color.

The predetermined surface attribute may be an edge, a convex surface portion, a concave surface portion, a planar part of the surface of the surgical registration device which is smaller than a predetermined minimum size, a part of the surface of the surgical registration device which is hidden underneath another part of the surgical registration device or else. At least one of the predetermined surface attributes and the predetermined color may be specified in the surface model data or may be specified in another data type obtained before matching the surface model to the part of the depth information.

Determining the second pose may comprise extracting information from the detected at least one optical pattern. For example, the information indicates at least one parameter chosen from a size of the at least one optical pattern, a shape of the at least one optical pattern, an identification data (ID) of the at least one optical pattern, a type of the at least one optical pattern, the location of the at least one optical pattern with respect to the surface of the surgical registration device, a type of the surgical registration device, a shape of the surface of the surgical registration device, a shape of the surface of the second part of the surgical registration device, and a known relative spatial relationship between the surgical registration device and a tracking system of a surgical navigation system. In one example, the information indicates another parameter.

In one variant, the surgical registration device comprises at least one colored area arranged on the surface of the surgical registration device, wherein the at least one colored area is different from the at least one optical pattern, and wherein determining the second pose comprises detecting the at least one colored area in the image, obtaining second location information indicating a location of the at least one colored area with respect to the surface of the surgical registration device, and determining the second pose further based on the detected at least one colored area and the second location information.

For example, a preliminary second pose is determined based on the detected at least one optical pattern, the surface model data and the first location information, and the preliminary second pose is corrected based on the detected at least one colored area and the second location information in order to determine the second pose. In another example, the second pose is determined in a single step based on the detected at least one optical pattern, the surface model data, the first occasion information, the detected at least one colored area and the second location information.

In one example, the surgical registration device comprises at least one colored area arranged on the surface of the surgical registration device, wherein determining the third pose comprises obtaining second location information indicating a location of the at least one colored area with respect to the surface of the surgical registration device, determining, based on the second pose, the surface model data and the second location information, an approximated surface model describing an estimation of the surface of at least the second part of the surgical registration device in the second pose as described by the depth information, and matching the approximated surface model to the depth information to determine the third pose. For example, the approximated surface model is matched to the depth information obtained by the depth sensor of the sensor device.

Obtaining the depth information may comprise obtaining a plurality of depth pixels, obtaining a plurality of image pixels from the image, registering the plurality of image pixels to the plurality of depth pixels, and determining, based on color values of the registered image pixels, and based on values of the registered depth pixels, corrected values of the depth pixels to determine the depth information. The depth information may comprise both the values of the (i.e., registered) depth pixels and the corrected values of the depth pixels.

The approximated surface model is for example matched to values of the depth pixels. In other words, the approximated surface model may be matched to the depth information comprising the values of the depth pixels. That is, the approximated surface model is for example matched to measured depth values obtained by the depth sensor as the depth information. The surface model on the other hand may be matched to the corrected values of the depth pixels. In other words, the surface model may be matched to the depth information comprising the corrected values of the depth pixels. That is, the surface model is for example matched to color-adjusted depth values obtained by correcting the measured depth values.

The second pose and the third pose may each describe a relative spatial relationship between the surgical registration device and a sensor device comprising at least one sensor configured to obtain at least one data chosen from the depth information and the image.

The method for example further comprises obtaining a known relative spatial relationship between the surgical registration device and a tracking system of a surgical navigation system, and determining, based on the third pose and the known relative spatial relationship, a relative spatial relationship between the sensor device and the tracking system.

The sensor device for example comprises a camera configured to obtain the image and a depth sensor configured to obtain the depth information. The sensor device may be an augmented reality device comprising a camera and a depth sensor. The tracking system of the surgical navigation system is for example an optical or an electromagnetic tracking system configured to track at least one tracking marker attached to a patient or a surgical instrument.

According to a second aspect, a surgical registration device for use in surgical navigation is provided. The surgical registration device comprises a surface, wherein at least a surface of a second part of the surgical registration device is configured to be described by depth information and to be described by surface model data. The surgical registration device further comprises at least one optical pattern arranged on the surface of the surgical registration device in a predetermined location and configured to be depicted in an image of at least a first part of the surgical registration device, and an interface unit configured to removably attach the surgical registration device in a predetermined spatial relationship to a tracking system of a surgical navigation system.

The surface is for example configured such that irrespective of an orientation of the surgical registration device with respect to a viewing direction, at least two parts of the surface of the surgical registration device can be seen in the viewing direction. In one example, the at least two parts lie in different planes and the different planes are for example not parallel to one another. Alternatively, the at least two parts of the surface may lie on different portions of a spherical part of the surface.

The at least one optical pattern may comprise a plurality of optical patterns. For example, each of the plurality of optical patterns is different. The plurality of optical patterns may comprise or consist of optical patterns which are distinguishable from one another. In this case, each of the plurality of optical patterns is for example arranged on a different planar part of the surface. These different planar parts of the surface are in one example not parallel to one another.

In one variant, the surgical registration device comprises at least one colored area on the surface of the surgical registration device, wherein the at least one colored area is different from the at least one optical pattern. The colored area may be a geometrical form colored in a single color, for example a circle, an ellipse, a triangle, a rectangle, a pentagon, a star, a company logo, a letter or else.

In another variant, the at least one colored area and the at least one optical pattern overlap with each other, for example at least partially. In this case, the at least one colored area may be equal to the at least one optical pattern.

The at least one colored area in one example comprises a plurality of colored areas. For example, each of the plurality of colored areas is different. The plurality of colored areas may comprise or consist of colored areas which are distinguishable from one another. Each of the plurality of colored areas may be arranged on a different planar part of the surface of the surgical registration device. These different planar parts of the surface are in one example not parallel to one another.

The surgical registration device is for example constructed as a component that can be repeatedly sterilized.

According to a third aspect, a processor is provided. The processor is configured to perform the method of the first aspect. In particular, the processor is configured to obtain an image of at least a first part of the surgical registration device in a first pose, detect the at least one optical pattern in the image, obtain surface model data describing a surface of at least a second part of the surgical registration device, obtain first location information indicating a location of the at least one optical pattern with respect to the surface of the surgical registration device and determine, based on the detected at least one optical pattern, the surface model data and the first location information, a second pose of the surface of the surgical registration device. The processor is further configured to obtain depth information describing three-dimensional coordinates of the surface of at least the second part of the surgical registration device in the first pose, and determine, based on the second pose, the surface model data and the depth information, a third pose of the surface of the surgical registration de-vice.

According to a fourth aspect, a sensor device is provided. The sensor device comprises an image sensor configured to acquire an image and a sensor configured to acquire at least one of depth information and depth pixels. The sensor device further comprises the processor of the third aspect. For example, the sensor device comprises a camera as the image sensor. As the sensor configured to acquire at least one of the depth information and the depth pixels, the sensor device may comprise a depth sensor. The depth sensor may comprise a stereo camera. In this case, one of the cameras of the stereo camera may be used as the image sensor. Alternatively, the sensor device may comprise a different depth sensor such as a light detection and ranging (LIDAR) sensor, a time of flight (TOF) sensor or else. The sensor device may further comprise a display configured to display navigation information, based on at least the third pose. The sensor device may be configured to track at least one tracking marker, for example using a stereo camera comprised in the sensor device. The sensor device may be an augmented reality device, for example a head-mounted display (HMD) such as HOLOLENS® or MAGIC LEAP ONE®.

According to a fifth aspect, a surgical navigation system is provided which comprises the surgical registration device of the second aspect, and a tracking system configured to track at least one tracking marker attached to a patient or a surgical instrument, wherein the surgical registration device is attached, by the interface unit, in a predetermined spatial relationship to the tracking system. The tracking system of the surgical navigation system may be an optical or an electromagnetic tracking system configured to track at least one of a patient and a surgical instrument, for example by tracking the at least one tracking marker attached to the patient or the surgical instrument.

According to a sixth aspect, a computer program is provided. The computer program comprises instructions which, when the program is executed by a processor, cause the processor to carry out the method of the first aspect. Alternatively or additionally, a computer program product may be provided, wherein the computer program product comprises instructions which, when the program is executed by a computer, cause the computer to carry out the steps of the method of the first aspect.

According to a seventh aspect, a computer-readable medium is provided. The computer-readable medium has stored thereon the computer program or the computer program product of the sixth aspect.

According to an eighth aspect, a data carrier signal is provided. The data carrier signal carries the computer program or the computer program product of the sixth aspect.

BRIEF DESCRIPTION OF THE DRAWINGS

Further details, advantages and aspects of the present disclosure will become apparent from the following embodiments taken in conjunction with the drawings wherein.

DETAILED DESCRIPTION

Figure 1:
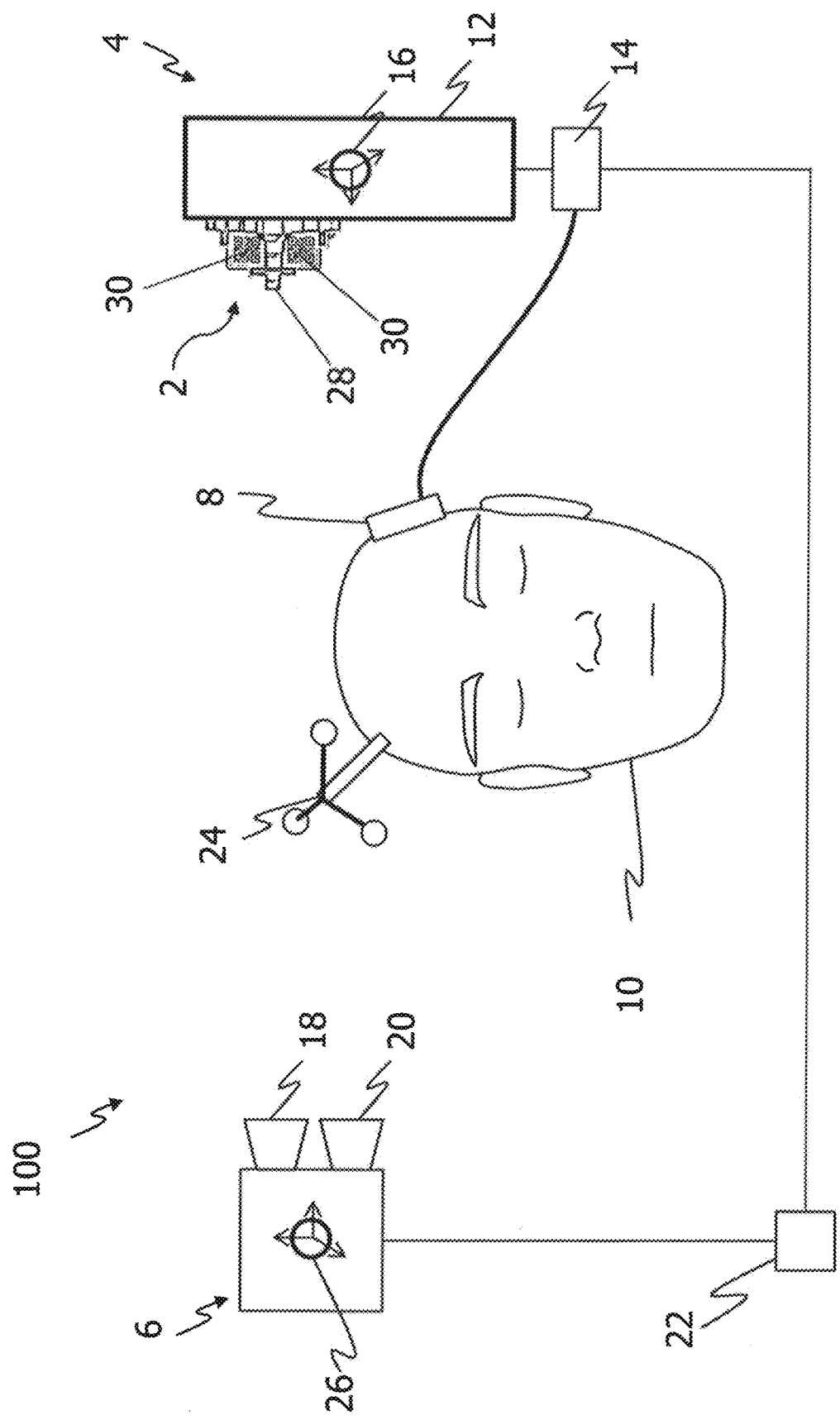
FIG. 1 shows an arrangement comprising a surgical registration device, a tracking system and a sensor device.

In the following description, exemplary embodiments of a surgical registration device, a processor, a computer program, a computer-readable storage medium, a data carrier signal, a sensor device, a surgical navigation system and a method of determining a pose of the surgical registration device will be explained with reference to the drawings. The same reference numerals will be used to denote the same or similar structural features or method steps.

FIG. 1 shows an arrangement 100, also referred to as a system 100, comprising a surgical registration device 2, a tracking system 4 and a sensor device 6. In the shown arrangement 100, the tracking system 4 is en electromagnetic tracking system. Of course, other types of tracking systems may be employed as the tracking system 4, for example an optical tracking system or an ultrasonic tracking system.

A first tracking marker 8 is attached to a body 10 of a patient. The tracking system 4 comprises an electromagnetic field generator 12 and a positioning unit 14. The electromagnetic field generator 12 is configured to generate an electromagnetic field which extends beyond at least a portion of the body 10. The first tracking marker 8 is an electromagnetic tracking marker. The first tracking marker 8 is configured to sense the generated electromagnetic field and to provide measurement data to the positioning unit 14. Based on the measurement data of the first tracking marker 8, the positioning unit 14 determines a position and orientation of the first tracking marker 8 in a tracking coordinate system 16. This enables tracking of the body 10 by the tracking system 4.

In case the tracking system 4 is an optical tracking system, the surgical registration device 2 is removably attached to an optical detection unit (not shown) of the tracking system 4 in a known spatial relationship. Such an optical detection unit is for example a stereo camera. In this case, the first tracking marker 8 is an optical tracking marker which can be tracked by the optical tracking system to determine a position and orientation of the first tracking marker 8 in the tracking coordinate system 16.

Of course, two tracking systems may be provided, for example the optical tracking system and the electromagnetic tracking system described above. In this case, one or more tracking markers attached to the body 10 may be provided for the electromagnetic tracking system and one or more tracking markers attached to the body 10 may be provided for the optical tracking system.

In the arrangement 100 shown in FIG. 1, the surgical registration device 2 is removably attached, by an interface unit comprised in the surgical registration device 2 (not shown), to the electromagnetic field generator 12 in a known spatial relationship. If the tracking system 4 is an optical tracking system, the surgical registration device 2 may be removably attached by the interface unit to the optical detection unit of the optical tracking system in a known spatial relationship. This means that a pose (position and orientation) of the surgical registration device 2 in the tracking coordinate system 16 is known. In a further variant, the surgical registration device 2 is arranged in a fixed spatial relationship to a third tracking marker (not shown) tracked by the tracking system 4. By determining a position and orientation of the third tracking marker in the tracking coordinate system 16, a pose (at least one of a position and an orientation) of the surgical registration device 2 in the tracking coordinate system 16 can be determined.

The sensor device 6 comprises a camera 18 as an image sensor, and a depth sensor 20 as a sensor configured to acquire at least one of depth information and depth pixels. A processor 22 is connected to the sensor device 6. The processor 22 may be arranged in the sensor device 6.

Optionally, a second tracking marker 24 may be arranged on the body 10. The second tracking marker 24 is an optical tracking marker. Based on images obtained by the camera 18, or based on stereo images of a stereo camera (not shown) comprised in the sensor device 6, a pose of the second tracking marker 24 may be determined by the processor 22 in the sensor device coordinate system 26, enabling a direct tracking of the patient by the sensor device 6. The provision of the second tracking marker 24 is however not necessary, as the pose of the surgical registration device 2 can be determined in the sensor device coordinate system 26, as will be laid out below in detail, wherein the pose of the surgical registration device 2 in the tracking coordinate system 16 is known. In other words, a registration between the sensor device coordinate system 26 and the tracking device coordinate system 16 can be derived such that a tracked pose of the patient in the tracking coordinate system 16 can be transformed into a pose in the sensor device coordinate system 26, enabling an indirect tracking of the patient by the sensor device 6 via the tracking system 4.

The surgical registration device 2 comprises a body 28 having a surface, and at least one optical pattern 30 arranged on the surface. The at least one optical pattern 30 is for example a two-dimensional black and white QR code. The at least one optical pattern 30 is arranged on the surface in a predetermined location. This means that a position and orientation of the at least one optical pattern 30 in the tracking coordinate system 16 is known. Also known are properties of the at least one optical pattern 30 such as a geometry, a pattern type, a size or else. One or more of these properties may be specific for one optical pattern and thus between different optical pattern may be detected in an image at least partly based on more of these properties.

The surgical registration device 2 comprises at least one colored area arranged on the surface (not shown). The colored area is for example a circle having a single color. The at least one colored area is arranged on the surface in a predetermined location. This means that a position and orientation of the at least one colored area in the tracking coordinate system 16 is known. Also known are properties of the at least one colored area such as a geometry, a color, a size or else. One or more of these properties may be specific for a given colored area and thus differ between different colored areas. The at least one colored area may be detected in an image at least partly based on one or more of these properties.

The processor 22 is configured to determine the pose of the surgical registration device 2 in the sensor device coordinate system 26. Subsequently, the transformation between the sensor device coordinate system 26 and the tracking coordinate system 16 can be determined by the processor 22, as the pose of the surgical registration device 2 is then known in both the tracking coordinate system 16 and the sensor device coordinate system 26. In the shown arrangement 100, the processor 22 is connected (i.e., with a wireless data connection) to the tracking system 4. The processor 22 may be configured to determine navigation information to be displayed to a surgeon, based on data received from the sensor device 6 and the tracking system 4. The processor 22 may further control the tracking system 4, for example by controlling the generation of the electromagnetic field by the electromagnetic field generator 12.

Figure 2:
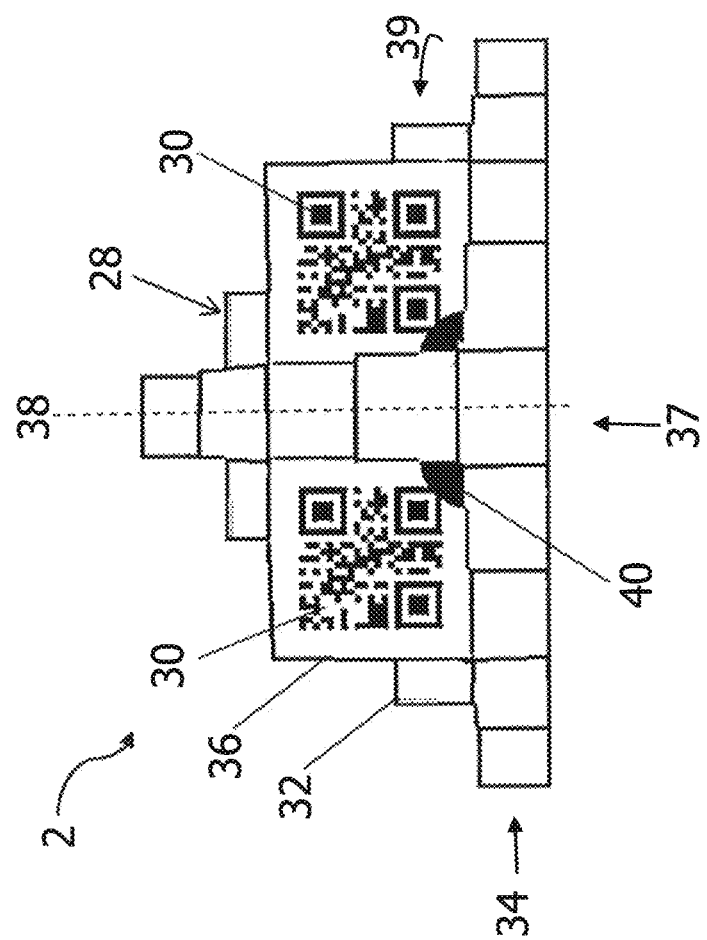
FIG. 2 shows a front view of a first example of the surgical registration device.

FIG. 2 shows a front view of a first example of the surgical registration device 2 of FIG. 1. As can be seen, the body 28 is formed by a plurality of cubes of different sizes. Of course, the body 28 can be formed as a solid body so that no cubes need to be joined with one another. In other words, the referral to cubes may only relate to the form of the surface of the surgical registration device 2. A plurality of small cubes 32 form a base plate 34, a middle plate 37 and a side plate 39. Two large cubes 36 are arranged on the base plate 34 adjacent to the side plate 39 and the middle plate 37. The at least one optical pattern 30 is disposed on each visible planar side of each large cube 36. In FIG. 2, only two optical patterns 30 are depicted due to the chosen front view of the surgical registration device 2. On the base plate 34, convex spherical sections 40 are disposed which each are in contact with one large cube 36, the base plate 34 and one of the middle plate 37 or the side plate 39. The surface of the surgical registration device 2 is mirror-symmetric to a virtual plane 38 which separates the middle plate 37 into two similar parts. The optical patterns 30 are not mirror-symmetric to one another. Preferably, the optical patterns 30 are different from one another. The overall form of the surface of the surgical registration device 2 can in this example be roughly described as a pyramid which has been cut in half.

The surface of the surgical registration device 2 is configured such that irrespective of an orientation of the surgical registration device 2 with respect to a viewing direction, at least two parts of the surface of the surgical registration device 2 can be seen in the viewing direction, wherein the at least two parts lie in different planes. For example, the surfaces of the small cubes 32 which form the base plate 34 lie in different planes. This results in different distances between the surface of the surgical registration device 2 and the depth sensor 20, independent of the relative pose of the surgical registration device 2 with respect to the depth sensor 20. In other words, it is possible to obtain different values of depth pixels, using the depth sensor 20, which describe the distance of the surface of the surgical registration device 2 to the depth sensor 20. It is advantageous that many contours of the surface are detectable by the depth sensor 20 instead of just one plane.

Figure 3:
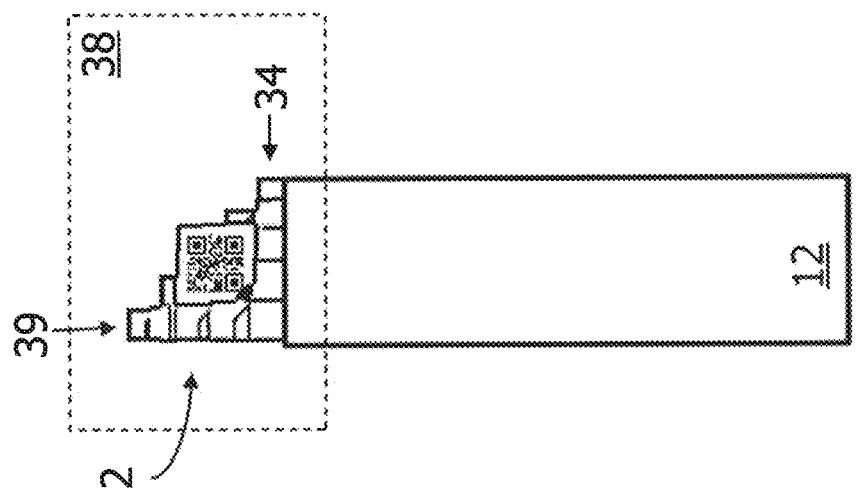
FIG. 3 shows a side view of the first example of the surgical registration device arranged on the tracking system.

FIG. 3 shows a side view of the first example of the surgical registration device 2 arranged on the tracking system 4 of FIG. 1. The surgical registration device 2 is removably attached to the electromagnetic field generator 12 of the tracking system 4 such that the base plate 34 is arranged on a top of the electromagnetic field generator. The surgical registration device 2 is removably connected to the electromagnetic field generator 12 by the interface unit (not shown) in a fixed spatial relationship. The surgical registration device 2 in this example is dimensioned such that it does cover the full width of the electromagnetic field generator 12. A side of the side plate 39 which faces away from the large cubes 36 is aligned with a side of the electromagnetic field generator 12. In this example, the electromagnetic field generator 12 with the attached surgical registration device 2 is to be arranged such that the at least one optical pattern 30 is detectable by the camera 18 of the sensor device 6.

Figure 4:
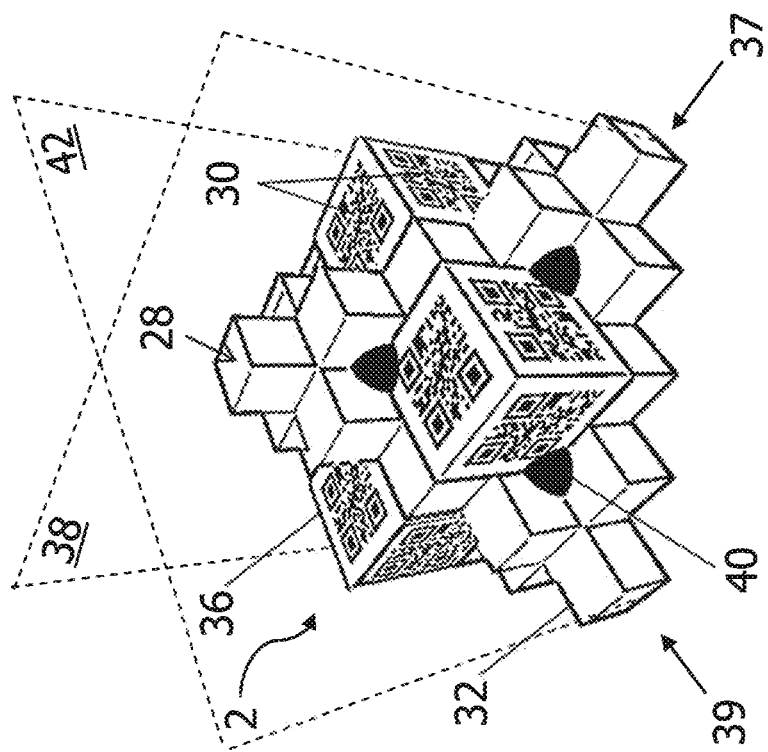
FIG. 4 shows a perspective view of a second example of the surgical registration device.

FIG. 4 shows a perspective view of a second example of the surgical registration device 2 of FIG. 1. The surgical registration device of this example also comprises several components already described with reference to FIGS. 2 and 3, a description of some of which is therefore omitted here. In difference to the first example of the surgical registration device 2, the overall form of the surface of the surgical registration device 2 can in the second example be roughly described as a pyramid. The body 28 of the surgical registration device is in the second example formed by four instead of two large cubes 36 and by a plurality of small cubes 32. The surface of the surgical registration device 2 is mirror-symmetric to the virtual plane 38 which separates the middle plate 37 into two similar parts. The surface of the surgical registration device 2 is also mirror-symmetric to a virtual plane 42 which separates the side plate 39 into two similar parts. It can be seen that the at least one optical pattern 30 comprises a plurality, in total twelve, optical patterns 30. Each of the plurality of optical patterns 30 is arranged on a different planar part of the surface. The different planar parts of the surface are not all parallel to one another. The optical patterns 30 are not only, but also disposed on different sides of the large cubes 36, which different sides are not parallel to one another. Although the optical patterns 30 shown are identical, they may differ from one another.

Figure 5:
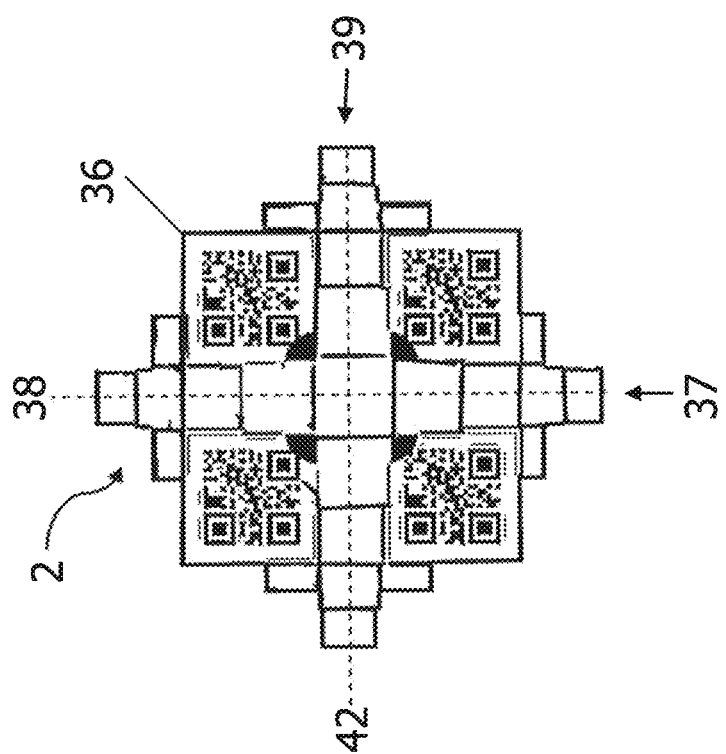
FIG. 5 shows a top view of the second example of the surgical registration device.

FIG. 5 shows a top view of the second example of the surgical registration device 2 described above with reference to FIG. 4. The optical patterns 30 are not mirror-symmetric to one another. Instead, the optical patterns 30 have the same orientation but different positions on the surface of the surgical registration device 2. Note that the optical patterns 30 preferably differ from one another, for example represent different QR codes.

Figure 6:
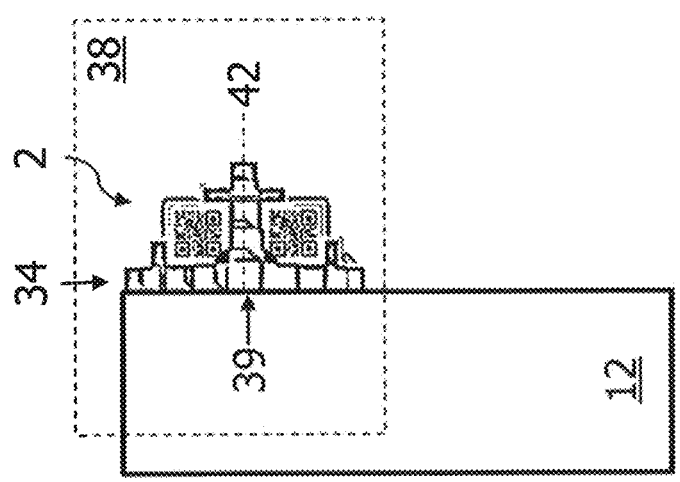
FIG. 6 shows a side view of the second example of the surgical registration device arranged on the tracking system.

FIG. 6 shows a side view of the second example of the surgical registration device 2 arranged on the electromagnetic field generator 12 of the tracking system 4 of FIG. 1. Also in this case, the surgical registration device 2 can be arranged on the electromagnetic field generator 12 by the interface unit (not shown). In the shown example, the surgical registration device 2 is arranged on a front side of the electromagnetic field generator 12 instead of the top side as shown in FIG. 3. Of course, the surgical registration device 2 may be arranged on another surface of the electromagnetic field generator 12 as long as the relative position between these two devices is known. Preferably, the surgical registration device 2 is arranged on the electromagnetic field generator 12 such that most of the surface of the surgical registration device 2 is detectable by the camera 18 and the depth sensor 20 of the sensor device 6.

Figure 7:
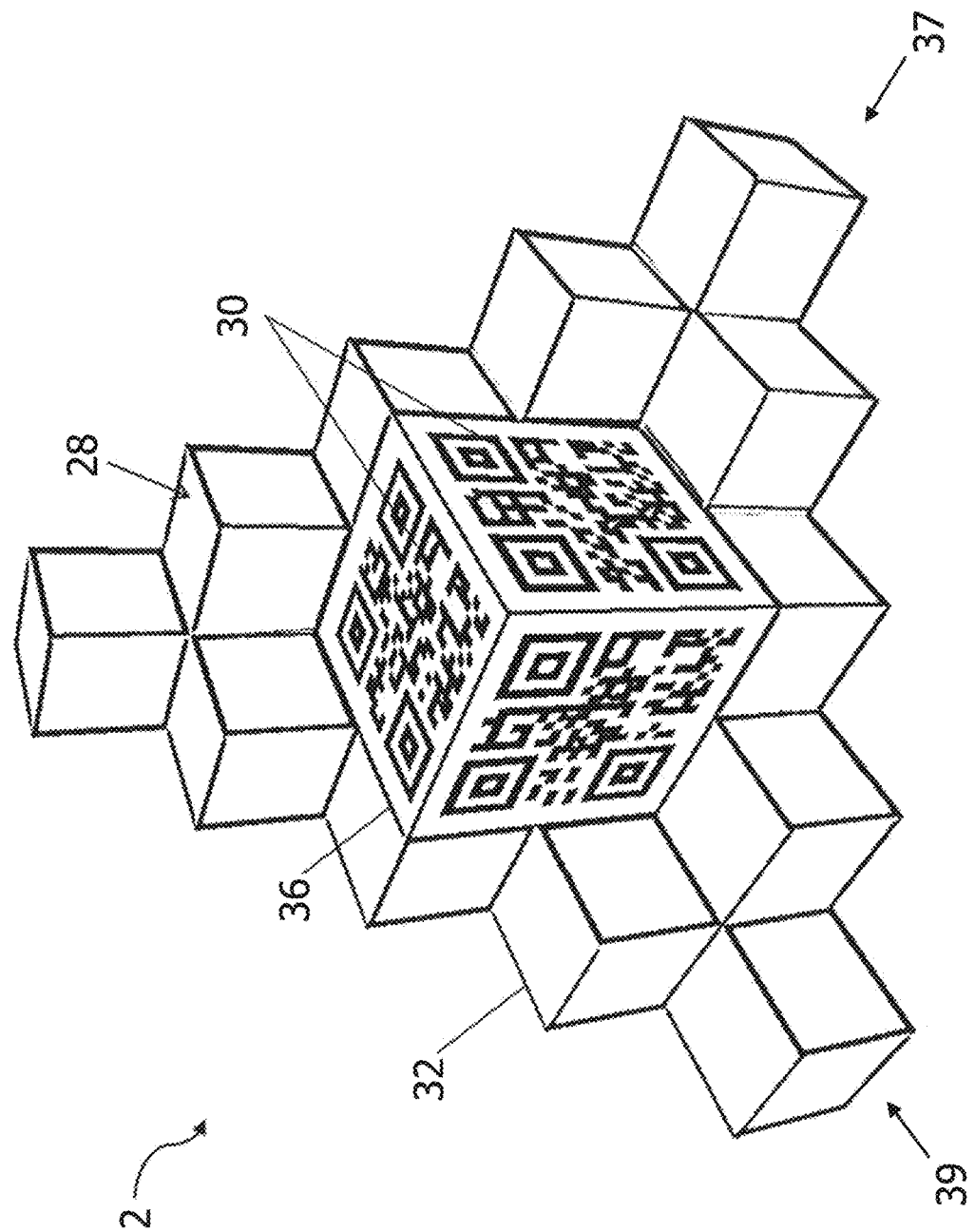
FIG. 7 shows a third example of the surgical registration device.

FIG. 7 shows a third example of the surgical registration device 2 of FIG. 1. The surgical registration device 2 of this example also comprises several components already described with reference to FIGS. 2 to 6, which will therefore not all be described again here. In this example, the overall form of the surface of the surgical registration device 2 can be roughly described as a quarter of a pyramid. The body 28 of the surgical registration device 2 is in this example formed by a plurality of small cubes 32 and one large cube 36. Three optical patterns 30 are disposed on three different sides of the large cube 36.

Figure 8:
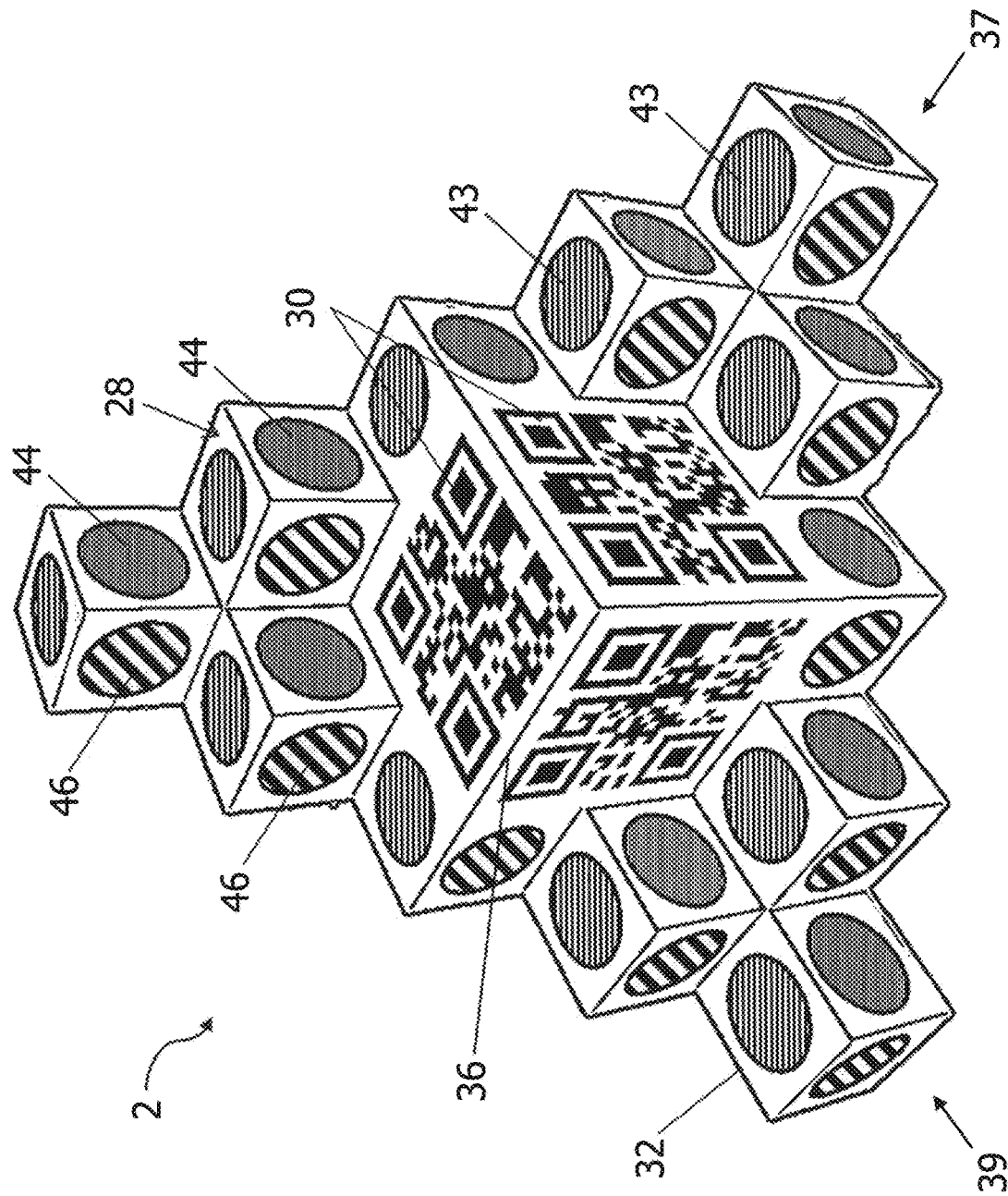
FIG. 8 shows a fourth example of the surgical registration device.

FIG. 8 shows a fourth example of the surgical registration device 2 of FIG. 1. The surgical registration device of this example also comprises several components already described with reference to FIGS. 2 to 7, which will not all be described again here. The surface of the surgical registration device 2 of the fourth example is the same as the surface of the surgical registration device 2 of the third example shown in FIG. 7. Each of the three visible planar sides of the large cube 36 is covered with an optical pattern 30. On the surface of the surgical registration device 2 of the fourth example, the at least one colored area is arranged. As can be seen in FIG. 8, the at least one colored area comprises a plurality of colored areas arranged on the surface of the surgical registration device 2. The at least one colored area is different from the at least one optical pattern 30. First colored areas 43 having a first color are arranged on top sides of the small cubes 32. Second colored areas 44 having a second color are arranged on right sides of the small cubes 32. Third colored areas 46 having a third color are arranged on left sides of the small cubes 32. The first, second and third colored areas 43, 44 and 46 are thus arranged on different planar parts of the surface of the surgical registration device 2, wherein the different planar parts of the surface are not all parallel to one another. The first, second and third colors may differ from one another. The surgical registration device 2 of the fourth example may be arranged on the electromagnetic field generator 12 of FIG. 1 as described above with reference to FIGS. 3 and 6.

Figure 9:
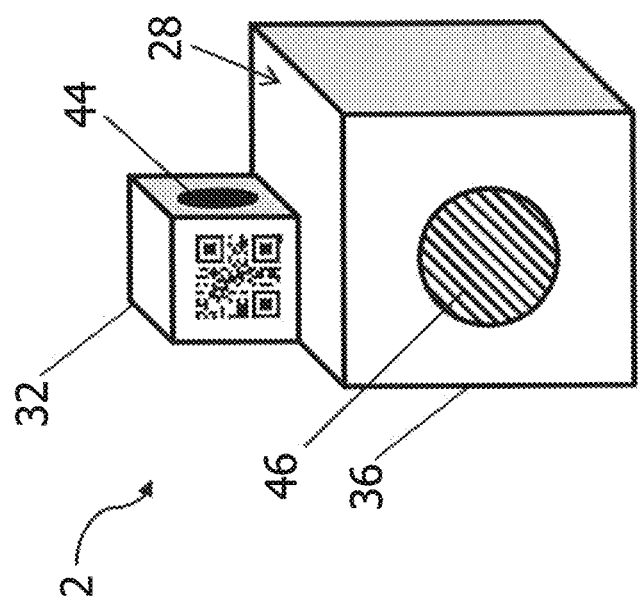
FIG. 9 shows a fifth example of the surgical registration device.

FIG. 9 shows a fifth example of the surgical registration device 2 of FIG. 1. The surgical registration device of this example also comprises several components already described with reference to FIGS. 2 to 8, a description of some of which is omitted here. In the fifth example of the surgical registration device 2, the body 28 of the surgical registration device 2 is formed by one large cube 36 and one small cube 32. The optical pattern 30 is arranged on a left side of the small cube 32. A second colored area 44 having the second color is arranged on a right side of the small cube 32. A third colored area 46 having the third color is arranged on a left side of the large cube 36. Also, the surgical registration device 2 of the fifth example may be arranged on the electromagnetic field generator 12 of FIG. 1 as described above with reference to FIGS. 3 and 6.

The surgical registration device 2 of FIGS. 1 to 8 is constructed as a component that can be repeatedly sterilized. For example, the surgical registration device 2 is formed as a solid component. The body 28 of the surgical registration device 2 may be formed as a rigid body, for example a molded component. The surgical registration device may comprise no movable parts. Edges of the surface of the surgical registration device 2 are for example rounded or blunted. The surgical registration device is made of a material which is resistant to repeated sterilization. The at least one optical pattern 30 and the at least one colored area are permanently formed on the surface of the surgical registration device, such that the at least one optical pattern 30 and the at least one colored area are still detectable after sterilization of the surgical registration device 2. For example, the at least one optical pattern 30 and the at least one colored area are covered by a protective transparent component of the surgical registration device 2 which is rigidly connected to the body 28 and which protects the at least one optical pattern 30 and the at least one colored area from being removed. Alternatively or additionally, the at least one optical pattern 30 and the at least one colored area are printed onto the surface of the surgical registration device 2 permanently.

Of course, features of one of the examples of the surgical registration device 2 described above with reference to FIGS. 2 to 9 may be combined with others of the examples described with reference to these figures. For instance, the surgical registration device 2 of the first example may comprise the second colored areas 44 of the fourth example, the surgical registration device of the third example may be formed with a pyramidal shape having a double mirror-symmetry as described with reference to the second example, and so on.

Next, a method according to the present disclosure will be described with reference to FIG. 10. The method may be performed by the processor 22 of FIG. 1. The method may be performed by the processor 22 comprised in the sensor device 6 which further comprises the camera 18 and the depth sensor 20. The method may be performed by a system comprising the processor 22 and the surgical registration device 2. The method may be performed by a system comprising the sensor device 6 which comprises the processor 22, wherein the system further comprises at least the surgical registration device 2.

In step 70, an image of at least a first part of the surgical registration device 2 in a first pose is obtained. The at least a first part comprises the at least one optical pattern 30 arranged on the surface of the surgical registration device 2. The first pose is a first position and orientation of the surgical registration device in the sensor device coordinate system 26. The first pose may also be referred to as real, exact or correct pose of the surgical registration device 2 in the sensor device coordinate system 26.

In step 72, the at least one optical pattern 30 is detected in the image. A pattern detection algorithm may be used in order to detect the optical pattern 30 in the image. For example, the type of the optical pattern 30 is known in advance to be a QR code in black and white, and the pattern detection algorithm searches the acquired image for any QR codes in black and white. In case the type of the optical pattern 30 is not known in advance, the pattern detection algorithm may search for patterns of different types such as barcodes, colored QR codes, black and white QR codes, or else.

The processor 22 may extract information from the detected optical pattern 30. This information for example indicates at least one parameter chosen from a size of the at least one optical pattern 30, a shape of the at least one optical pattern 30, an ID of the at least one optical pattern 30, a type of the at least one optical pattern 30, the location of the at least one optical pattern 30 with respect to the surface of the surgical registration device 2, for example in a model coordinate system, a type of the surgical registration device 2, a shape of the surface of the surgical registration device 2, a shape of the surface of the second part of the surgical registration device 2, and a known relative spatial relationship between the surgical registration device 2 and the tracking system 4, for example between the surgical registration device 2 and the electromagnetic field generator 12.

Based on the detection of the at least one optical pattern 30 in the image, the processor 22 determines a position and orientation of the detected optical pattern 30 in the sensor device coordinate system 26, for example using a homography algorithm. For example, the real size and shape of the detected optical pattern 30 on the surface of the surgical registration device 2 is known or extracted as information from the detected optical pattern 30. Based on the size and shape of the detected optical pattern 30 in the image and the real size and shape of the optical pattern 30 on the surface of the surgical registration device 2, the processor 22 can determine the position and orientation of the detected optical pattern 30 in the sensor device coordinate system 26.

In step 74, surface model data is obtained. The surface model data describes a surface of at least a second part of the surgical registration device 2. The surface of the second part of the surgical registration device 2 is part of the surface of the surgical registration device 2. The second part may be different from the first part, may be partly identical with the first part or may be equal to the first part. The surface model for example is an arithmetic definition of the surface of at least the second part, a three dimensional mesh representing the surface of at least the second part, a point cloud representing the surface of at least the second part or three-dimensional image data of at least the second part. The surface model data describes the surface of at least the second part of the surgical registration device 2 in the model coordinate system.

In step 76, first location information is obtained which indicates a location of the at least one optical pattern 30 with respect to the surface of the surgical registration device 2. The first location information indicates the location of the at least one optical pattern 30 as a position and orientation in the model coordinate system. Alternatively, the first location information may indicate the location of the at least one optical pattern 30 by defining properties of the surface at the location of the at least one optical pattern 30. In this case, the first location information may define that the at least one optical pattern 30 is arranged on a planar part of the surface, on a rectangular plane of the surface, on a spherical portion of the surface, on a plane adjacent to a large cube 36 forming the surface, or else.

In step 78, a second pose of the surface of the surgical registration device 2 is determined based on the detected at least one optical pattern 30, the surface model data and the first location information. In particular, a position and orientation of the detected at least one optical pattern 30 is determined in the sensor device coordinate system 26, as described above. As the location of the detected at least one optical pattern 30 on the surface of the surgical registration device 2 is known from the first location information, and as the surface of the surgical registration device 2 is known from the surface model data, the processor 22 can determine the second pose of the surface of the surgical registration device 2. The second pose is a second position and orientation of the surface of the surgical registration device 2 in the sensor device coordinate system 26. The second pose thus describes a relative spatial relationship between the surgical registration device 2 and the sensor device 6. The second pose may be referred to as optically detected pose, pose obtained by analysis of the image, image-based pose, or else.

As noted above, the at least one colored area may be different from the at least one optical pattern 30. In this case, different positions and orientations of colored areas and optical patterns 30 can be used in order to increase the accuracy of the second pose.

In particular, determining the second pose may comprise detecting the at least one colored area in the image. The at least one colored area may be detected in the image based on a pattern detection algorithm, a color filter applied to the image, a search for pixels in the image that have a color value that lies in a predetermined range or else. Based on known properties of the at least one colored area, for example a size and shape of the at least one colored area, the processor 22 may determine a position and orientation of the detected at least one colored area in the sensor device coordinate system 26, for example using a homography algorithm.

Determining the second pose may then further comprise obtaining second location information indicating a location of the at least one colored area with respect to the surface of the surgical registration device 2. The second location information indicates the location of the at least one colored area as a position and orientation in the model coordinate system. Alternatively, the second location information may indicate the location of the at least one colored area by defining properties of the surface at the location of the at least one colored area. In this case, the second location information may define that the at least one colored area is arranged on a planar part of the surface, on a rectangular plane of the surface, on a spherical portion of the surface, on a plane adjacent to a large cube 36 forming the surface, or else.

The second pose may then be determined also based on the detected at least one colored area and the second location information.

In one variant, a preliminary second pose is determined based on the detected at least one colored area, the second location information and the surface model data. In particular, a position and orientation of the detected at least one colored area is determined in the sensor device coordinate system 26, as described above. As the location of the detected at least one colored area on the surface of the surgical registration device 2 is known from the second location information, and as the surface of the surgical registration device 2 is known from the surface model data, the processor 22 can determine the preliminary second pose of the surface of the surgical registration device 2. The preliminary second pose is a preliminary position and orientation of the surface of the surgical registration device 2 in the sensor device coordinate system 26. The preliminary second pose may then be corrected based on the detected at least one optical pattern 30 and the first location information to determine the second pose.

In another variant, the preliminary second pose is determined based on the detected at least one optical pattern 30, the first location information and the surface model data and the preliminary second pose is then corrected based on the detected at least one colored area and the second location data to determine the second pose.

In a further variant, no preliminary second pose is determined. In this case, the second pose may be determined based on the detected at least one optical pattern 30, the first location information, the detected at least one colored area, the second location information and the surface model. For example, the determined pose of the detected at least one optical pattern 30 in the sensor device coordinate system 26 and the determined pose of the at least one colored area in the sensor device coordinate system 26 can be matched to the surface described by the surface model data using a point-to-surface matching algorithm or a surface-to-point matching algorithm. As a result of the matching, the second pose of the surface of the surgical registration device 2 can be obtained.

In step 80, depth information describing three-dimensional coordinates of the surface of at least the second part of the surgical registration device 2 in the first pose is obtained. The three-dimensional coordinates of the surface of at least the second part of the surgical registration device 2 are described in the sensor device coordinate system 26 by the depth information. The depth information may be a depth image of at least the second part of the surgical registration device 2, a three-dimensional mesh representing the surface of at least the second part of the surgical registration device 2, a point cloud representing points which lie on the surface of at least the second part of the surgical registration device 2 or else. As in the case of the obtained image, the first pose is the first position and orientation of the surgical registration device 2 in the sensor device coordinate system 26. For example, the depth information is acquired by the depth sensor 20 and the image is acquired by the camera 18 at the same time. Alternatively, the depth information and the image are obtained at different points in time, when the surgical registration device 2 has a certain spatial relationship to the sensor device 6, which relationship can be described by the first pose.

Measurement results of depth sensors are often influenced by colors of a detected object. Depending on the colors of the detected object, it may be determined as being closer to or farther from the depth sensor 20 than it is in reality. In other words, the depth pixels may not describe correct three-dimensional coordinates, as the depth sensor 20 is sensitive to color. In view of this assertion, obtaining the depth information may comprise several steps.

In one step, a plurality of depth pixels may be obtained. Each depth pixel describes three-dimensional coordinates of a single point or area lying on the surface of at least the second part of the surgical registration device 2. These three-dimensional coordinates are described in the sensor device coordinate system 26. The depth pixels may be obtained using the depth sensor 20 of the sensor device 6. For example, the depth sensor 20 is a TOF camera which obtains a depth image, wherein each pixel comprised in the depth image is a depth pixel. The depth sensor 20 may alternatively comprise a stereo camera that acquires two images. The depths sensor 20 or the processor 22 may then determine a depth image, also referred to as parallax image, based on images acquired by the stereo camera. Also in this case, each pixel comprised in the depth image is a depth pixel. Of course, the depth pixels may describe the three-dimensional coordinates in a depth sensor coordinate system different from the sensor device coordinate system 26. A known transformation between these two coordinate systems may then be used to transform the coordinates from the depth sensor coordinate system to the sensor device coordinate system 26.

In another step, a plurality of image pixels may be obtained from the image. Each of the image pixels has a color value, in case the image is a color image. The image pixels may define color values of pixels in the sensor device coordinate system 26. Of course, the image pixels may describe the color values in a camera coordinate system different from the sensor device coordinate system 26. A known transformation between these two coordinate systems may be then be used to transform the coordinates from the camera coordinate system to the sensor device coordinate system 26.

In a subsequent step, the plurality of image pixels may be registered to the plurality of depth pixels. One or more known transformations between the camera coordinate system, the depth sensor coordinate system, and the sensor device coordinate system 26 may be used to transform the plurality of image pixels and the plurality of depth pixels to a common frame of reference, for example into the sensor device coordinate system 26. The registration of the plurality of image pixels to the plurality of depth pixels may be referred to as inter-camera registration. As a result of the registration, a registered depth image may be obtained, in which each depth pixel is registered with an image pixel (i.e., a correlated image pixel) having a certain color value.

In a further step, the depth information may be determined by determining corrected values of the depth pixels based on color values of the registered image pixels, and based on values of the registered depth pixels. Predetermined offsets associated with different color values can be used for this purpose. These offsets may be obtained by the processor 22 as part of the depth information, the surface model data or a separate data.

For example, a first depth pixel has a value of $\{x1, y1, z1\}$ which describes three-dimensional coordinates of a point, which lies on the surface of the surgical registration device 2, in the sensor device coordinate system 26. The first depth pixel is then registered by the processor 22 to a first image pixel having a color value of $\{R1, Y1, B1\}$. The processor 22 may then select a predetermined offset of $\{a1, b1, c1\}$ associated with the color value of $\{R1, Y1, B1\}$ from data obtained by the processor 22. Subsequently, the processor 22 can apply the offset $\{a1, b1, c1\}$ to the value $\{x1, y1, z1\}$ of the first depth pixel to determine a corrected value $\{x1+a1, y1+b1, z1+c1\}$ of the first depth pixel.

In another example, the predetermined offset comprises a fix offset of $\{a1, a2, a3\}$ and a depth-dependent offset of $\{d1, e1, f1\}$. In this case, by applying the predetermined offset to the first depth pixel, a corrected value of $\{x1*d1+a1, y1*e1+b1, z1*f1+c1\}$ of the first depth pixel is obtained.

Usually, the predetermined offset only describes an offset in a viewing direction from the depth sensor, such as an offset of $\{0, 0, c1\}$ or a fix offset of $\{0, 0, c1\}$ and a depth-dependent offset of $\{0, 0, f1\}$.

By correcting the values of all depth pixels obtained from a depth image, the processor 22 can obtain a corrected depth image. The corrected depth image may also be referred to as color-calibrated depth image, offset-adjusted depth image, color-shifted depth image, or else. The corrected values of the depth pixels, for example in the form of the corrected depth image, may then be used as the depth information.

In step 82, a third pose of the surface of the surgical registration device is determined, based on the second pose, the surface model data and the depth information. The third pose is a third position and orientation of the surgical registration device 2 in the sensor device coordinate system 26. The third pose thus describes a relative spatial relationship between the surgical registration device 2 and the sensor device 6. The third pose may also be referred to as corrected second pose, improved second pose, adjusted second pose, final pose, or else.

The third pose may be determined by the processor 22 by determining, based on the second pose and based on the surface model data, a surface model describing the surface of at least the second part of the surgical registration device 2 in the second pose. The surface model is determined by transforming the surface described by the surface model data from the model coordinate system to the sensor device coordinate system 26, based on the determined second pose. The surface model describes the surface of at least the second part of the surgical registration device 2 in the sensor device coordinate system 26.

In a next step, the surface model may be matched to the depth information to determine the third pose. For example, a surface matching algorithm is used in order to match the three-dimensional coordinates in the sensor device coordinate system 26, which three-dimensional coordinates are described by the depth information, to the surface described by the surface model. As a result of the matching, the second pose may be changed, corrected, adjusted or corrected to the third pose. Whilst the second pose is only determined based on the image, the third pose is furthermore determined based on the depth information. In other words, the third pose is determined based on measurements of two sensors using different sensor principles, namely based on measurements of an image sensor such as the camera 18 and a sensor such as the depth sensor 20.

In an example, the surface model is matched to a part of the depth information which fulfills at least one criterion chosen from: not representing a predetermined surface attribute; not representing an object other than the surgical registration device; and not representing a part of the surgical registration device which has a predetermined color. The predetermined surface attribute may be an edge, a convex surface portion, a concave surface portion, a planar part of the surface of the surgical registration device 2 which is smaller than a predetermined minimum size, a part of the surface of the surgical registration device 2 which is hidden underneath another part of the surgical registration device 2 or else. At least one of the predetermined surface attributes and the predetermined color may be specified in the surface model data or may be specified in another data type obtained before matching the surface model to the part of the depth information. The surface model may be matched to the part of the depth information by removing all content of the depth information apart from the part of the depth information and then matching the three-dimensional coordinates in the sensor device coordinate system 26, which three-dimensional coordinates are described by the remaining depth information, to the surface described by the surface model. Alternatively, all content of the depth information apart from the part of the depth information may be ignored for the matching.

As noted above, measurement results of depth sensors are often influenced by colors of a detected object. Depending on the colors of the detected object, it may be determined as being closer to or farther from the depth sensor 20 than it is in reality. In other words, the depth pixels may not describe correct three-dimensional coordinates, as the depth sensor 20 is sensitive to color. This effect can be used in order to improve the accuracy of the determined third pose.

In particular, determining the third pose may comprise obtaining the second location information indicating the location of the at least one colored area with respect to the surface of the surgical registration device 2. The second location information in this case also comprises an indication of a color value of the at least one colored area.

Determining the third pose may then further comprise a step of determining, based on the second pose, the surface model data and the second location information, an approximated surface model. The approximated surface model describes an estimation of the surface of at least the second part of the surgical registration device 2 in the second pose as described by the depth information. The approximated surface model in particular describes an estimation of the surface of at least the second part of the surgical registration device 2 in the second pose as described by the values of the depth pixels. The approximated surface model is determined by transforming the surface described by the surface model data from the model coordinate system to the sensor device coordinate system 26 based on the second pose. The second location information is used to identify locations of colored areas on the surface of surface model in the sensor device coordinate system 26 and their respective color values. Subsequently, a predetermined offset is applied to the at least one colored area depending on its respective color value. As described above, the predetermined offsets may be obtained as part of the surface model data, the second location information or as separate data by the processor 22.

By applying the predetermined offset to the at least one colored area, the surface model is deformed. In particular, a region of the surface described by the surface model in which the at least one colored area lies is shifted into a certain direction and by a certain amount as defined by the applied offset. As a result, the surface model is changed such that, depending on the color values and the predetermined offsets associated therewith, some or all of the regions of the surface described by the surface model in which the at least one colored area lies are offset compared to the surface of the surface model. In other words, the approximated surface model is generated based on the knowledge that depth sensors are influenced by color values. The approximated surface model is an estimation of the surface of the surgical registration device 2 as it will be detected by the depth sensor 20. The approximated surface model is determined such that it matches the values of the depth pixels better than the surface model. The approximated surface model may thus also be referred to as color-corrected surface model, color-adjusted surface model, depth pixel value estimation model, or else.

In a further step, the approximated surface model may be matched to the depth information to determine the third pose. For example, a surface matching algorithm is used in order to match the three-dimensional coordinates in the sensor device coordinate system 26, which three-dimensional coordinates are described by the depth information, to the surface described by the approximated surface model. The approximated surface model is preferably matched to the values of the depth pixels. In other words, the approximated surface model is preferably matched to uncorrected, raw-data or measured depth values comprised in the depth information. The surface model on the other hand is preferably matched to the corrected values of the depth pixels. In other words, the surface model is preferably matched to corrected, adjusted or color-calibrated depth values comprised in the depth information, for example to the color-calibrated depth image.

As noted above, the third pose is also determined based on other information. In particular, the third pose is determined based on the second pose, the surface model data and the depth information. It may further be determined based on the matching of the surface model to the depth information and/or based on the matching of the approximated surface model to the depth information. Either is one or more preliminary third pose determined based on some of the aforementioned information and then corrected based on the remaining of the information or the third pose is determined at once based on all of the information described above as being used for determining the third pose.

The method may further comprise a step of obtaining a known relative spatial relationship between the surgical registration device 2 and the tracking system 4 of a surgical navigation system, in particular a pose of the surgical registration device 2 in the tracking coordinate system 16.

As a further step, the method may comprise determining, based on the third pose and the known relative spatial relationship, a relative spatial relationship between the sensor device and the tracking system. In other words, a transformation may be determined by the processor 22 between the sensor device coordinate system 26 and the tracking coordinate system 16 based on the determined third pose and the known pose of the surgical registration device 2 in the tracking coordinate system 16.

Figure 10:
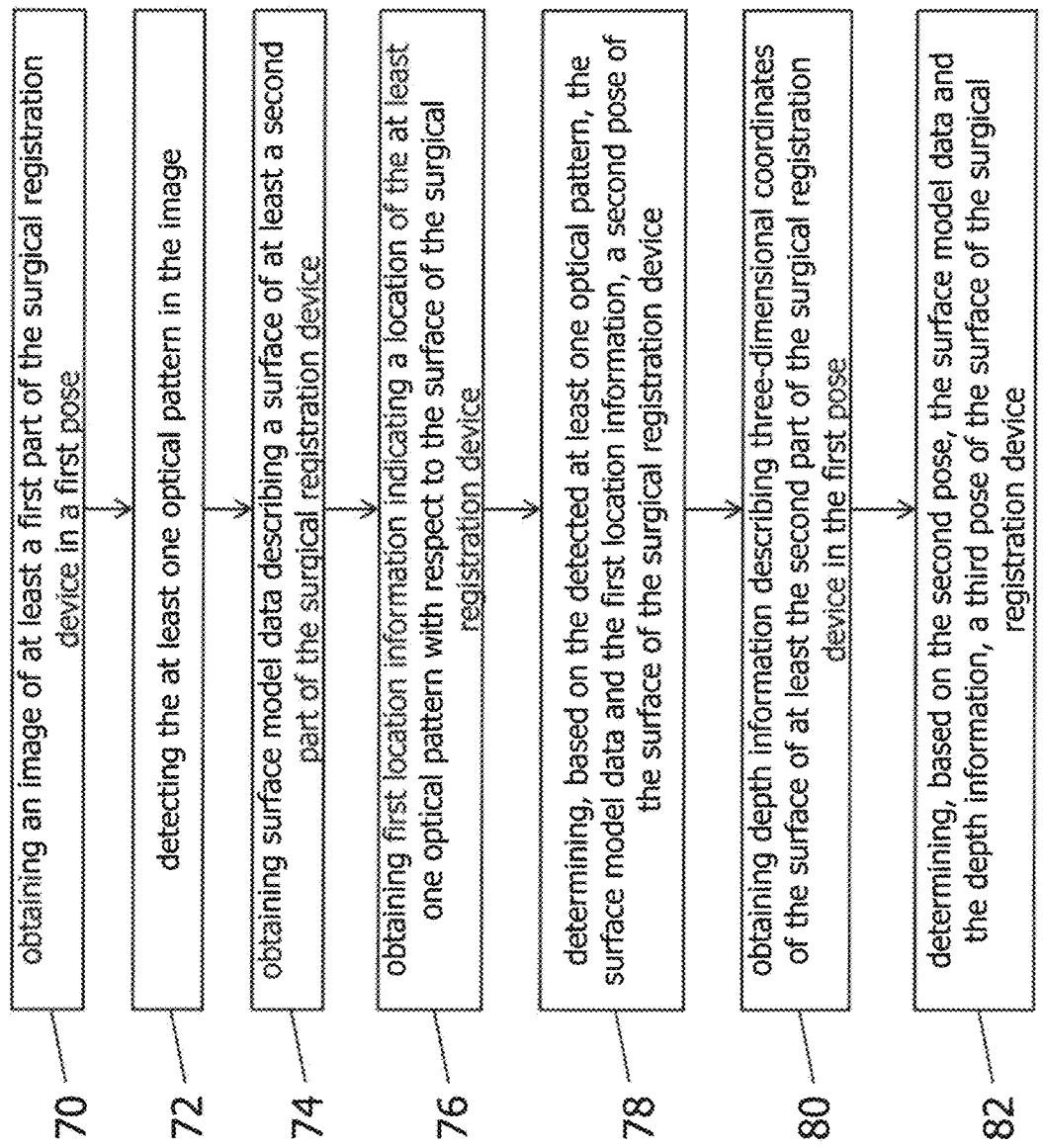
FIG. 10 shows a flow diagram of a method described herein.
Figure 11:
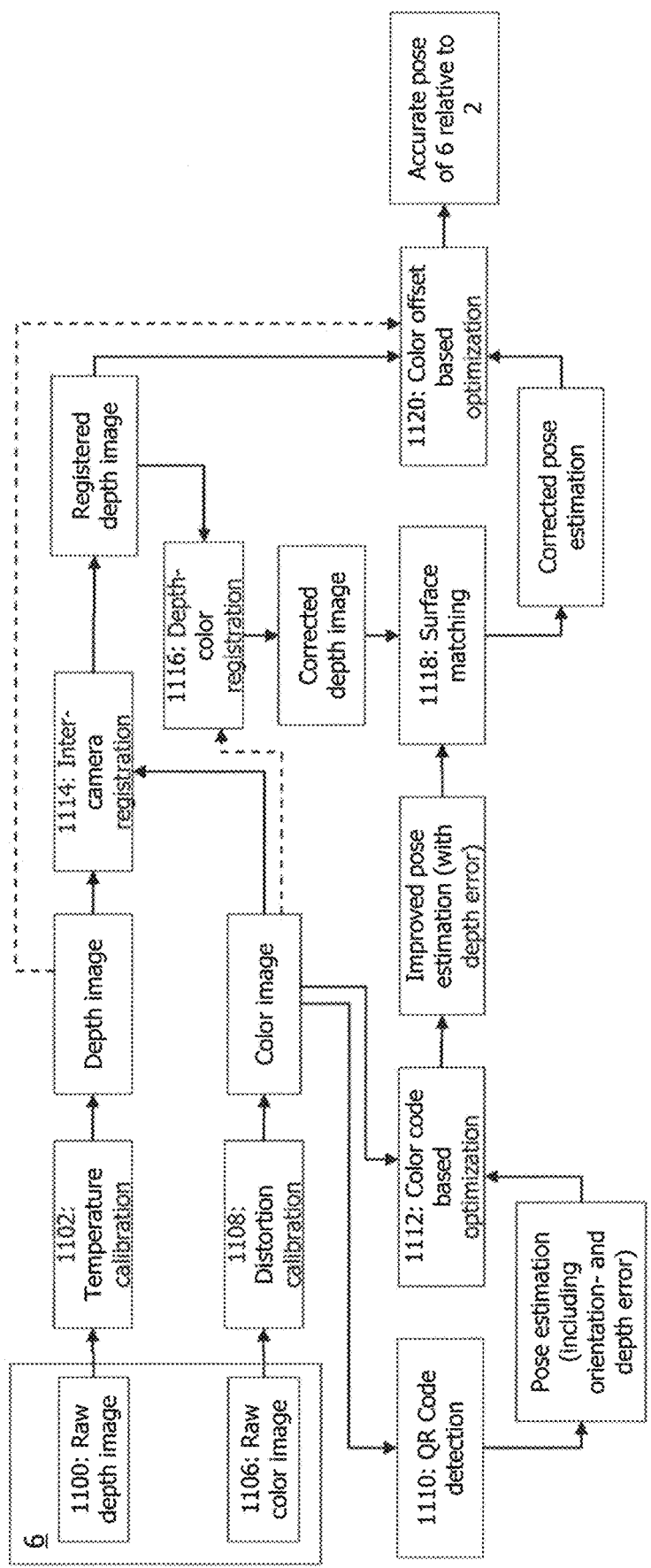
FIG. 11 shows another flow diagram of the method of FIG. 10.

FIG. 11 shows another flow diagram of the method of FIG. 10. Most steps shown in FIG. 11 were already described with reference to FIG. 10, although different reference signs are used in both figures. The sensor device 6 acquires a raw depth image in step 1100. A temperature calibration is performed in step 1102 based on the raw depth image in order to obtain the depth image comprising the depth pixels. The temperature calibration removes temperature-based errors from the raw depth image resulting from a temperature-dependency of measurements by the depth sensor. The sensor device 6 further acquires a raw color image in step 1106. A distortion calibration is performed in step 1108 order to obtain the image, in this case the color image. The distortion calibration removes distortion-based errors from the raw color image resulting from distortion by optical components or sensor errors of the image sensor used to acquire the raw color image. In step 1110, the at least one optical pattern 30, in the shown example a QR code, is detected in the color image. Based on the surface model data, the first location information and the detected at least one optical pattern 30, a pose estimation is determined. The pose estimation typically includes an orientation- and a depth error. In order to improve the pose estimation, a color code based optimization may be performed in step 1112. In this step, the at least one colored area is detected and the second location information is obtained. Then, based on the detected at least one colored area and based on the second location information, the pose estimation is improved to determine an improved pose estimation. The improved pose estimation may contain a depth error.

In case step 1112 is omitted, the pose estimation corresponds to the second pose. In case step 1112 is performed, the improved pose estimation corresponds to the second pose. In case the improved pose estimation corresponds to the second pose, the pose estimation may correspond to the preliminary second pose. Of course, steps 1110 and 1112 may be performed in combination without determining the pose estimation by directly determining the improved pose as the second pose.

In step 1114, the image pixels of the color image are registered to the depth pixels of the depth image during the inter-camera registration in order to determine the registered depth image. The registered depth image may comprise the depth pixels and information describing a correlation of each depth pixel to the image pixels. In step 1116, the corrected values of the depth pixels are determined in order to obtain the corrected depth image. The corrected values are determined based on the values of the depth pixels comprised in the registered depth image and based on the color values of the pixels of the color image, using the information describing the correlation of each depth pixel to the image pixels. Alternatively, the registered depth image also comprises the color values of the registered image pixels.

In step 1118, the surface model, which is determined based on the surface model data and the second pose, is matched to the corrected depth image by a surface matching algorithm. Note that the surface matching in step 1118 may be performed based on the second pose, the surface model data and the depth image, for example in case one or both of steps 1114 and 1116 are omitted. As a result of the surface matching, a corrected pose estimation is obtained which should no longer include a depth error. In one variant, only steps 1110 and 1118 are performed. In this case, the depth image and the pose estimation may be used for the surface matching in step 1118 instead of the corrected depth image and the improved pose estimation.

In step 1120, a color offset based optimization is performed. In particular, the approximated surface model is determined and matched to the depth information using the values of the depth pixels. As can be seen, the approximated surface model may be determined after determining the registered depth image or directly after determining the depth image. As a result of step 1120, an accurate pose of the sensor device 6 relative to the surgical registration device 2 is determined. In one variant, only steps 1110 and 1120 are performed. In this case, the approximated surface model and the pose estimation may be used for the color offset based optimization in step 1120 instead of the approximated surface model and the corrected pose estimation.

In case the method finishes after step 1118, the corrected pose estimation corresponds to the third pose. In case the method finishes after step 1120, the accurate pose of the sensor device 6 relative to the surgical registration device 2 corresponds to the third pose. Of course, the determination of the corrected pose estimation may be omitted by performing the surface matching step 1118 together with the color offset based optimization step 1120.

It is clear from the flowchart of FIG. 11 that some steps may be omitted and/or the sequence of some steps may be changed. For example, step 1112 may be performed before step 1110. One or more of steps 1112, 1114 and 1116 may be omitted. Alternatively or additionally, one of steps 1118 and 1120 may be omitted.

The method described herein can, as noted above, be performed by the processor 22. The present disclosure also relates to a computer program comprising instructions which, when the program is executed by a processor such as the processor 22, cause the processor to carry out the method described herein, for example with reference to FIGS. 10 and 11. Furthermore, the current disclosure relates to a computer-readable medium having stored thereon the computer program, and to a data carrier signal carrying the computer program.

The surgical registration device 2 described herein is formed such that its pose can be determined with high accuracy by the sensor device 6. The surgical registration device 2 described herein is formed such that a plurality of surface features such as edges, planar parts, spherical parts and more can be detected by the depth sensor 20 of the sensor device 6 which is for example an augmented reality device, augmented reality glasses or else. At the same time, the surgical registration device 2 comprises the at least one optical pattern 30. The position and orientation of the surgical registration device 2 can be determined precisely as the third pose by using an optical detection of the at least one optical pattern 30 and further using a spatial detection of the surface of the surgical registration device 2 by the depth sensor 20. In other words, two different tracking types, namely optical tracking and depth-based tracking, are used in order to determine the third pose. This increases the accuracy of the determined third pose.

Still further, the surgical registration device 2 may comprise the at least one colored area. The third pose can therefore be improved further by taking into account detected positions of the at least one colored area.

Also, a color dependency of the values of the depth pixels can be used to further improve the determined third pose. According to one approach, the depth image may be corrected based on color values of pixels registered to the depth pixels of the depth image. The corrected depth image can then be matched to the surface model, leading to an improved matching result and a higher accuracy of the third pose. According to another approach, the color dependency of the values of the depth pixels is compensated for by determining the approximated surface model and matching the approximated surface model with the depth image.

The features described in relation to the exemplary embodiments shown in the drawings can be readily combined to result in different embodiments. It is apparent, therefore, that the present disclosure may be varied in many ways. Such variations are not to be regarded as a departure from the scope of the invention as defined by the claims appended hereto.

The invention claimed is:

1. A computer-implemented method of determining a pose of a surgical registration device, wherein the surgical registration device comprises a surface and at least one optical pattern arranged on the surface, the method comprising:
   obtaining an image of at least a first part of the surgical registration device in a first pose;
   detecting the at least one optical pattern in the image;
   obtaining surface model data describing a surface of at least a second part of the surgical registration device;
   obtaining first location information indicating a location of the at least one optical pattern with respect to the surface of the surgical registration device;
   determining, based on the at least one optical pattern, the surface model data and the first location information, a pose of the surface of the surgical registration device;
   obtaining depth information describing three-dimensional coordinates of the surface of at least the second part of the surgical registration device in the first pose; and
   determining, based on the determined pose of the surface of the surgical registration device, the surface model data and the depth information, an adjusted pose of the surface of the surgical registration device; and
   wherein the determined pose of the surface of the surgical registration device and the adjusted pose of the surface of the surgical registration device each describe a relative spatial relationship between the surgical registration device and a sensor device comprising at least one sensor configured to obtain at least one data chosen from the depth information and the image;
   wherein determining the pose of the surface of the surgical registration device comprises extracting information from the detected at least one optical pattern, the information indicating a known relative spatial relationship between the surgical registration device and a tracking system of a surgical navigation system; and
   wherein the method further comprises determining, based on the adjusted pose of the surface of the surgical registration device and the known relative spatial relationship between the surgical registration device and the tracking system, a relative spatial relationship between the sensor device and the tracking system.

2. The method of claim 1, wherein determining the adjusted pose of the surface of the surgical registration device comprises:
   determining, based on the determined pose of the surface of the surgical registration device and based on the surface model data, a surface model describing the surface of at least the second part of the surgical registration device in the determined pose of the surface of the surgical registration device; and
   matching the surface model to the depth information to determine the adjusted pose of the surface of the surgical registration device.

3. The method of claim 2, wherein the surface model is matched to a part of the depth information which fulfills at least one criterion chosen from:
   not representing a predetermined surface attribute;
   not representing an object other than the surgical registration device; and
   not representing a part of the surgical registration device which has a predetermined color.

4. The method of claim 3, wherein the predetermined surface attribute is at least one of an edge, a convex surface portion, a concave surface portion, a planar part of the surface of the surgical registration device which is smaller than a predetermined minimum size, and a part of the surface of the surgical registration device which is hidden underneath another part of the surgical registration device.

5. The method of claim 1, wherein determining the pose of the surface of the surgical registration device further comprises extracting information from the detected at least one optical pattern, the information indicating at least one parameter chosen from
   a size of the at least one optical pattern,
   a shape of the at least one optical pattern,
   an identification data, ID, of the at least one optical pattern,
   a type of the at least one optical pattern,
   the location of the at least one optical pattern with respect to the surface of the surgical registration device,
   a type of the surgical registration device,
   a shape of the surface of the surgical registration device.

6. The method of claim 1, wherein the surgical registration device comprises at least one colored area arranged on the surface of the surgical registration device, wherein the at least one colored area is different from the at least one optical pattern, and wherein determining the pose of the surface of the surgical registration device comprises:
   detecting the at least one colored area in the image;
   obtaining second location information indicating a location of the at least one colored area with respect to the surface of the surgical registration device; and
   determining the pose of the surface of the surgical registration device further based on the detected at least one colored area and the second location information.

7. The method of claim 1, wherein obtaining the depth information comprises:
   obtaining a plurality of depth pixels;
   obtaining a plurality of image pixels from the image;
   registering the plurality of image pixels to the plurality of depth pixels; and
   determining, based on color values of the registered image pixels, and based on values of the registered depth pixels, corrected values of the depth pixels to determine the depth information.

8. The method of claim 1, wherein the surgical registration device comprises at least one colored area arranged on the surface of the surgical registration device, wherein determining the adjusted pose of the surface of the surgical registration device comprises:
obtaining second location information indicating a location of the at least one colored area with respect to the surface of the surgical registration device;
determining, based on the determined pose of the surface of the surgical registration device, the surface model data and the second location information, an approximated surface model describing an estimation of the surface of at least the second part of the surgical registration device in the determined pose of the surface of the surgical registration device as described by the depth information; and
matching the approximated surface model to the depth information to determine the adjusted pose of the surface of the surgical registration device.

9. A processor configured to:
obtain an image of at least a first part of a surgical registration device in a first pose;
detect at least one optical pattern in the image;
obtain surface model data describing a surface of at least a second part of the surgical registration device;
obtain first location information indicating a location of the at least one optical pattern with respect to the surface of the surgical registration device;
determine, based on the at least one optical pattern, the surface model data and the first location information, a determined pose of the surface of the surgical registration device;
obtain depth information describing three-dimensional coordinates of the surface of at least the second part of the surgical registration device in the first pose; and
determine, based on the determined pose of the surface of the surgical registration device, the surface model data and the depth information, an adjusted pose of the surface of the surgical registration device; and
wherein the determined pose of the surface of the surgical registration device and the adjusted pose of the surface of the surgical registration device each describe a relative spatial relationship between the surgical registration device and a sensor device comprising at least one sensor configured to obtain at least one data chosen from the depth information and the image;
wherein determining the determined pose of the surface of the surgical registration device comprises extracting information from the detected at least one optical pattern, the information indicating a known relative spatial relationship between the surgical registration device and a tracking system of a surgical navigation system; and
wherein the processor is further configured to determine, based on the adjusted pose of the surface of the surgical registration device and the known relative spatial relationship between the surgical registration device and the tracking system, a relative spatial relationship between the sensor device and the tracking system.

10. A computer-implemented method of determining a pose of a surgical registration device, wherein the surgical registration device comprises a surface and at least one optical pattern arranged on the surface, the method comprising:
obtaining an image of at least a first part of the surgical registration device in a first pose, the first pose describing a position and an orientation of the surgical registration device;
detecting the at least one optical pattern in the image;
obtaining surface model data describing a surface of at least a second part of the surgical registration device;
obtaining first location information indicating a location of the at least one optical pattern with respect to the surface of the surgical registration device;
determining, based on the at least one optical pattern, the surface model data and the first location information, a second pose, the second pose describing a position and an orientation of the surface of the surgical registration device;
obtaining depth information describing three-dimensional coordinates of the surface of at least the second part of the surgical registration device in the first pose; and
determining, based on the second pose, the surface model data and the depth information, a third pose, the third pose describing an adjusted position or an adjusted orientation of the surface of the surgical registration device; and
wherein the second pose and the third pose each describe a relative spatial relationship between the surgical registration device and a sensor device comprising at least one sensor configured to obtain at least one data chosen from the depth information and the image,
wherein determining the second pose comprises extracting information from the detected at least one optical pattern, the information indicating a known relative spatial relationship between the surgical registration device and a tracking system of a surgical navigation system, and
wherein the method further comprises determining, based on the third pose and the known relative spatial relationship between the surgical registration device and the tracking system, a relative spatial relationship between the sensor device and the tracking system.

11. The method of claim 10, wherein the first part of the surgical registration device and the second part of the surgical registration device are different.

12. The method of claim 10, wherein the first part of the surgical registration device and the second part of the surgical registration device are partially identical or the same.

13. The method of claim 10, wherein the surface includes at least one colored area arranged on the surface;
wherein the at least one colored area is different from the at least one optical pattern;
wherein determining the second pose includes:
detecting the at least one colored area in the image;
obtaining second location information indicating a location of the at least colored area with respect to the surface of the surgical registration device; and
determining the second pose further based upon the detected at least one colored area and the second location information.

14. The method of claim 10, wherein the surgical registration device comprises at least one colored area arranged on the surface of the surgical registration device; and
wherein determining the third pose includes:
obtaining second location information indicating a location of the at least one colored area with respect to the surface of the surgical registration device;
determining, based on the second pose, the surface model data and the second location information, an approximated surface model describing an estimation of the surface of at least the second part of the surgical registration device in the second pose as described by the depth information; and matching the approximated surface model to the depth information to determine the third pose.

\* \* \* \* \*